US007662158B2

(12) United States Patent
Robinson

(10) Patent No.: US 7,662,158 B2
(45) Date of Patent: Feb. 16, 2010

(54) WIRE TWISTING DRIVER TOOL

(76) Inventor: Merle W. Robinson, P.O. Box 538, 571 N. Weaver, Hesston, KS (US) 67062

( * ) Notice: Subject to any disclaimer, the term of this patent is extended or adjusted under 35 U.S.C. 154(b) by 324 days.

(21) Appl. No.: 11/105,659

(22) Filed: Apr. 14, 2005

(65) Prior Publication Data

US 2006/0231276 A1 Oct. 19, 2006

(51) Int. Cl.
*A61B 17/58* (2006.01)

(52) U.S. Cl. .................................................... 606/104

(58) Field of Classification Search .................. 173/11, 173/13, 140, 14; 7/118, 128, 129, 107, 164; 81/438, 439, 440, 120, 121.1, 124.2, 124.4, 81/125.1, 176.2, 177.4; 30/161; 606/104; 264/148; 140/117, 118, 120, 149
See application file for complete search history.

(56) References Cited

U.S. PATENT DOCUMENTS 1,845,951 A * 2/1932 Worsham .................... 140/119
1,961,246 A * 6/1934 Powers ....................... 279/102
2,775,276 A * 12/1956 Rossner ..................... 81/177.1
2,810,415 A * 10/1957 Johnson ......................... 81/28
3,333,609 A 8/1967 Fielding
4,074,732 A 2/1978 Wilkens
4,865,086 A 9/1989 Robinson et al.
5,205,006 A * 4/1993 Panasuk ........................ 7/108
5,379,809 A 1/1995 Waulk
5,752,551 A 5/1998 Trueblood
5,832,796 A 11/1998 Chopra
5,887,631 A * 3/1999 Eaton ......................... 140/118
5,918,337 A 7/1999 Evling et al.
6,041,833 A 3/2000 Suric
6,922,887 B1 * 8/2005 Keswani ...................... 29/757
7,051,392 B2 * 5/2006 Dominguez .................... 7/164
2003/0150062 A1 8/2003 Muirhead

* cited by examiner

*Primary Examiner*—Pedro Philogene
(74) *Attorney, Agent, or Firm*—Kenneth H. Jack; Davis & Jack, LLC

(57) ABSTRACT

A screw or nut driver having a handle having front and rear ends; a driver shaft having front and rear ends, the driver shaft being fixedly attached to or formed wholly with the handle, the driver shaft extending forwardly from the front end of the handle; a driver head fixedly attached to or formed wholly with the front end of the driver shaft; a first rearwardly opening bore extending forwardly into the handle from the rear end of the handle; a socket having front and rear ends, the socket being nestingly received within the first rearwardly opening bore; a second rearwardly opening bore extending forwardly into the socket from its rear end; at least a first radially opening bore extending radially outwardly from the second rearwardly opening bore; and at least a first traction pin nestingly received by and extending radially inwardly from the at least first radially opening bore.

14 Claims, 6 Drawing Sheets

WIRE TWISTING DRIVER TOOL

FIELD OF THE INVENTION

This invention relates to hand tools; particularly electricians' hand tools. More particularly, this invention relates to such tools which include special adaptations for working with and manipulating electrical wires.

BACKGROUND OF THE INVENTION

Electricians commonly work with and manipulate insulated electrical wiring within and about electrical circuit and junction boxes. Wiring contacts which are presented upon electrical equipment contained within electrical junction boxes commonly comprise helically threaded electrode posts. Such posts commonly receive ring tongue terminals or spade tongue terminals of insulated electrical wiring. Upon engagement of such wire end terminals with such threaded electrodes, an electrician will typically threadedly mount matching helically threaded "hex" nuts over the electrodes, such nuts securing the terminals upon the electrodes. For final tightening of such hex nuts, the electrician commonly will utilize a nut driver tool for threadedly turning and compressively mounting the nut and the terminal over the electrode. Equipment housed within such electrical junction boxes also commonly present plate electrodes having helically threaded apertures therethrough, such apertures commonly receiving a helically threaded screw. In use of such apertured plate electrode and screw combinations, an electrician will typically align the eye or slot of a ring tongue or a spade tongue electric wire terminal with the helically threaded aperture, and the electrician will extend the shaft of such matchingly threaded screw through the eye or slot, and thence into the aperture. Thereafter, the electrician typically threadedly turns and mounts the screw within the aperture. Thereafter, the electrician will commonly finally tighten the screw against the terminal and against the electrode, securely electrically connecting the terminal upon the electrode. Such electrician will typically utilize a common screw driver for accomplishing such final screw tightening step.

Opposite ends of insulated wiring joined with equipment within electrical junction boxes as are described above are commonly electrically interconnected by helically intertwining the ends of such wires. Such stripped wire ends, upon helical twisting, create a substantially cylindrical wire tail which is suitable for extension into the bore of a plastic twist-on wire connector . In many circumstances, the gauge or thickness of the wires to be helically wound and formed into such cylindrical wire tail is such that the wires are difficultly manipulated and bent by finger pressure. Accordingly, an electrician desirably utilizes some tool which assists in helically intertwining such wires. As discussed above, electricians commonly have in hand a nut driver or a screw driver for securing wire terminals upon electrical equipment. However, common configurations of nut drivers and screw drivers typically lend no assistance in helically intertwining wires. Such electrician may inconveniently set aside or holster such driver tools, and the electrician may thereafter retrieve and utilize, for example, common pliers for twisting and helically intertwining the wires. However, the use of pliers for helically intertwining wires is undesirably cumbersome and awkward, such use undesirably tends to gouge and break stripped wire ends, and such use undesirably requires time consuming steps of retrieving and replacing tools which are different from the screw or nut driver wire connecting tools discussed above.

The instant inventive wire twisting driver tool solves or ameliorates problems discussed above by structurally adapting the handle portion of such driver tools as discussed above for additionally helically intertwining wires.

BRIEF SUMMARY OF THE INVENTION

A major structural component of the instant inventive wire twisting driver tool comprises a handle which is preferably configured similarly with that of a common screw or nut driver handle. Preferably, the handle element is composed of dielectric or electrically insulating plastic. Suitably, the handle may alternately comprise a hardwood or a silicon based composite material which is typically sufficiently dielectric.

A further structural component of the instant inventive wire twisting driver tool comprises a driver shaft which preferably comprises a hardened or tempered steel bar. Attaching means for interconnecting a rear end of the driver shaft with a forward end of the handle are preferably provided, such means preferably integrally molding the rear end of the driver shaft into and as a part of the forward end of the preferred plastic handle. Suitably, such attaching means may alternately comprise a steel square bored socket which is molded integrally within the front end of the handle, such socket functioning in combination with and nestingly receiving a square pin configuration of the rear end of the driver shaft. Such alternate nesting square socket and square pin driver shaft attaching means may be advantageously adapted for facilitating interchanges of different driver shafts for use with a singular handle. Other driver shaft attaching means such as tang, slot, and shear rivet combinations may similarly be suitably substituted.

A further structural component of the instant inventive wire twisting driver tool comprises at least a first driver head such as common or a Phillips screw driving blade, either of which may be formed wholly with the front end of the driver shaft. Alternately, the driver head may comprise an interchangeable nut driving socket.

A further structural component of the instant inventive wire twisting driver tool comprises at least a first rearwardly opening wire end receiving bore which preferably extends forwardly into the handle from the handle's rear end. Preferably, such rearwardly opening bore is fitted for receipt therein of a plurality of stripped wire ends which are in need of helical intertwining.

A further structural component of the instant inventive wire twisting driver tool comprises at least a first traction pin fixedly attached to or formed wholly with the handle, the at least first traction pin having an inner end, the inner end of the at least first traction pin extending radially into the rearwardly opening bore. Preferably, the at least first traction pin is configured as a blunt ended lug. Suitably, the at least first traction may be alternately configured as a pointed spike.

In use of the instant inventive wire twisting driver tool, an electrician may grasp the handle element in one hand while grasping a bundle of electrical wires having the insulation stripped from their ends. Thereafter, the electrician may extend the stripped ends of such wires forwardly into the tool's rearwardly opening bore until the at least first traction pin engages such wires, the at least first traction pin preferably extending interstitially between a pair of the wires. Thereafter, the electrician may manually counter-rotate the handle and the wire bundle about their longitudinal axes approximately three complete turns. While such counter-rotation progresses, the traction pin tends to frictionally bias against and apply rotational torque to the wires, causing the wires to twist helically about themselves within the rearwardly opening bore. Thereafter, the electrician may rearwardly withdraw the newly helically interconnected wire tail. Thereafter, the electrician may protectively cover the helically interconnected wire tail with an insulating twist-on wire connector.

Where the handle element of the instant invention comprises dielectric plastic or wood, the at least first traction pin element may suitably be supported by such material and may extend radially and inwardly from such material, the rearwardly opening bore extending directly into such material. However, for additional structural strength for supporting the at least first traction pin, the handle is preferably stratified annularly about the handle's longitudinal axis, such strata preferably comprising inner and outer stratums. The inner stratum preferably comprises aluminum or steel, such inner stratum extending annularly about and forming and defining the wire receiving rearwardly opening bore. Also, where such steel or aluminum inner stratum is provided, the at least first traction pin is preferably compression fitted into a radially extending pin receiving channel. Where the traction pin element is compression fitted into a pin receiving channel, as described above, the traction pin advantageously comprises a roll pin having a "C" shaped cross-sectional profile for frictionally spring biasing against the wall of the pin receiving channel. Suitably, the traction pin may alternately be formed wholly with the steel or aluminum inner stratum.

Where the preferred steel or aluminum inner stratum is provided, such stratum is preferably configured as a cylindrical wire end receiving socket. Such socket is preferably nestingly received within a rearwardly opening socket receiving bore or first bore which preferably extends forwardly into the handle from the handle's rear end. Preferably, such wire receiving socket or inner stratum element has a front end which is positioned rearwardly from the rear end of the driver shaft, such positioning beneficially allowing the preferred dielectric handle material to electrically insulate the driver shaft from the inner stratum or socket.

In order to allow the rearwardly opening bore element of the instant inventive wire twisting driver tool to accommodate and helically intertwine varying gauges of wire and varying numbers of wires, the socket's rearwardly opening bore element, or second bore, is preferably annularly coffered so that it presents a forward narrow bore section (for accommodating and intertwining smaller gauge or less numerous wires) and a rearward wide bore section (for accommodating and intertwining larger gauge or more numerous wires). Where such preferred annularly coffered configuration is provided, first and second traction pins are also preferably provided, such pins preferably being mounted as described above for respective radially inward extensions into such forward and rearward sections.

Accordingly, objects of the instant invention include the provision of a wire twisting driver tool having structural components as described above, wherein such structural components are arranged for the performance of functions as described above.

Other and further objects, benefits, and advantages of the instant invention will become known to those skilled in the art upon review of the Detailed Description of a Preferred Embodiment set forth below, and upon review of the appended drawings.

DETAILED DESCRIPTION OF A PREFERRED EMBODIMENT

Figure 1:
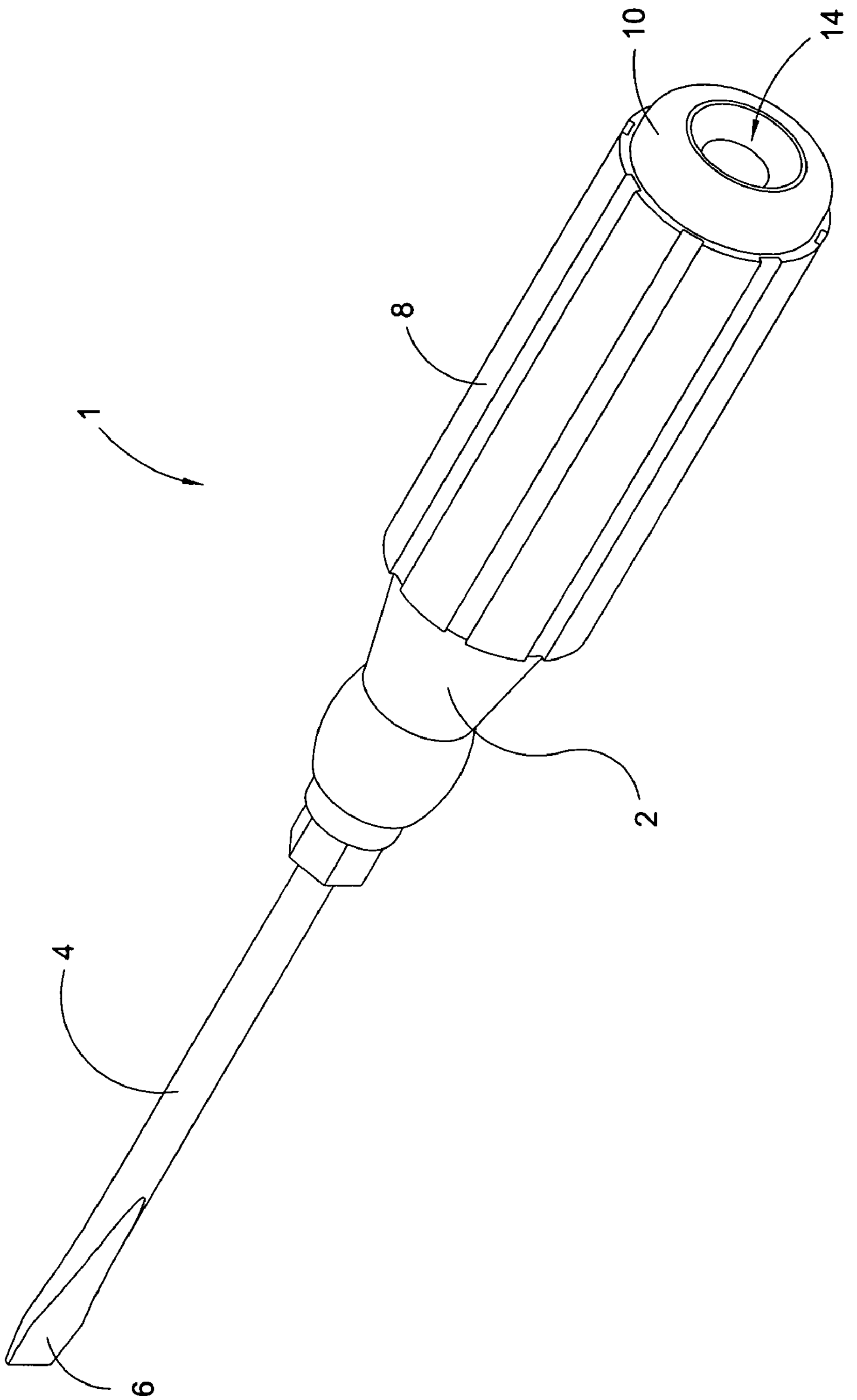
FIG. 1 is an isometric view of a preferred embodiment of the instant inventive wire twisting driver tool.

Referring now to the drawings, and in particular to FIG. 1, a preferred embodiment of the instant inventive wire twisting driver tool is referred to generally by Reference Arrow 1. The wire twisting driver tool 1 has a handle 2 which is preferably composed of a material having a high dielectric strength such as wood or plastic. For additional hand gripping friction and for additional electrical insulation, an elastomeric sleeve 8 preferably extends longitudinally along and annularly about handle 2.

Referring further to FIG. 1, a driver shaft 4, preferably composed of hardened steel, is provided. The rear end of the driver shaft 4 is preferably fixedly attached to the front end of handle 2. Such fixed attachment preferably integrally molds the rear end of driver shaft 4 into and as a part of the front end of handle 2. A driver head 6 is fixedly attached to or is formed wholly with the front end of driver shaft 4. The depiction in FIG. 1 of the driver head 6 as a common screw driving blade is representative of other common driver heads such as Phillips heads, Allen or "hex" heads, and nut driving sockets.

Figure 2:
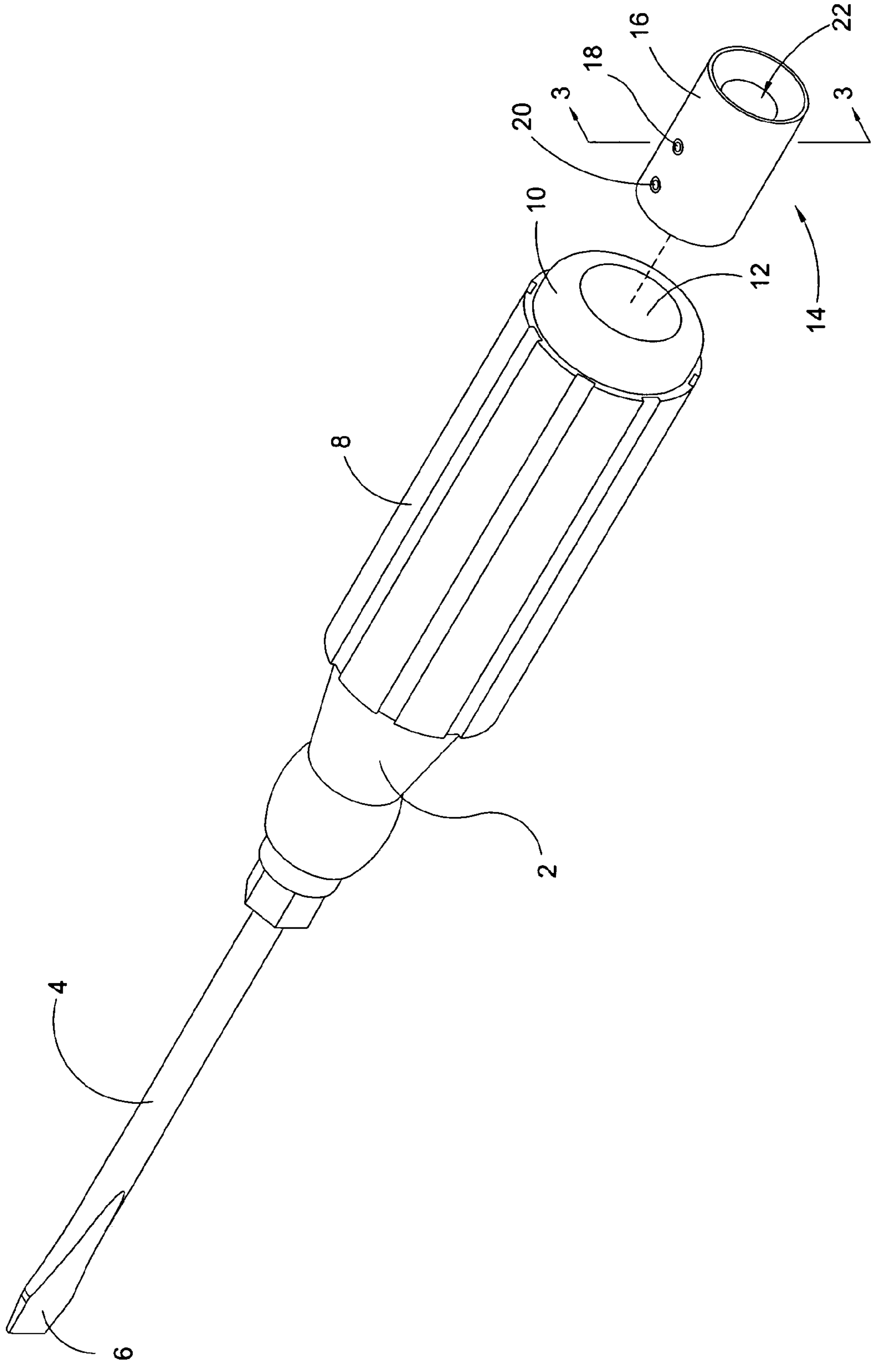
FIG. 2 is a partially exploded view of the tool of FIG. 1.

Referring simultaneously to FIGS. 1 and 2, the rear end 10 of handle 2 preferably presents a rearward opening of a first bore 12, such rearwardly opening bore 12 preferably extending forwardly therefrom into the handle 2. Preferably, the rearwardly opening bore 12 is closely fitted for sliding receipt of a socket 14. Upon forward insertion, preferably by compression driving, of socket 14 into bore 12, socket 14 is securely and fixedly attached to the rear end 10 of handle 2. Suitably and alternately, an adhesive may be interposed between the walls of the bore 12 and socket 14 for fixedly interconnecting the socket 14 and the handle 2. Also suitably and alternately, the socket 14 may, like the rear end of the forwardly extending driver shaft 4, be molded integrally with the handle 2.

Where a socket 14 and a handle 2 are provided in configurations consistent with those depicted in FIGS. 1 and 2, the handle 2 is effectively annularly stratified about its longitudinal axis, the socket 14 constituting an inner stratum, and the dielectric material of handle 2 extending annularly about socket 14 comprising an outer stratum. The rear end of driver shaft 4 preferably is positioned forwardly from the front end of socket 14, such displacement of structural ends advantageously allowing the dielectric handle material to electrically insulate the driver shaft 4 from the socket 14.

Figure 3:
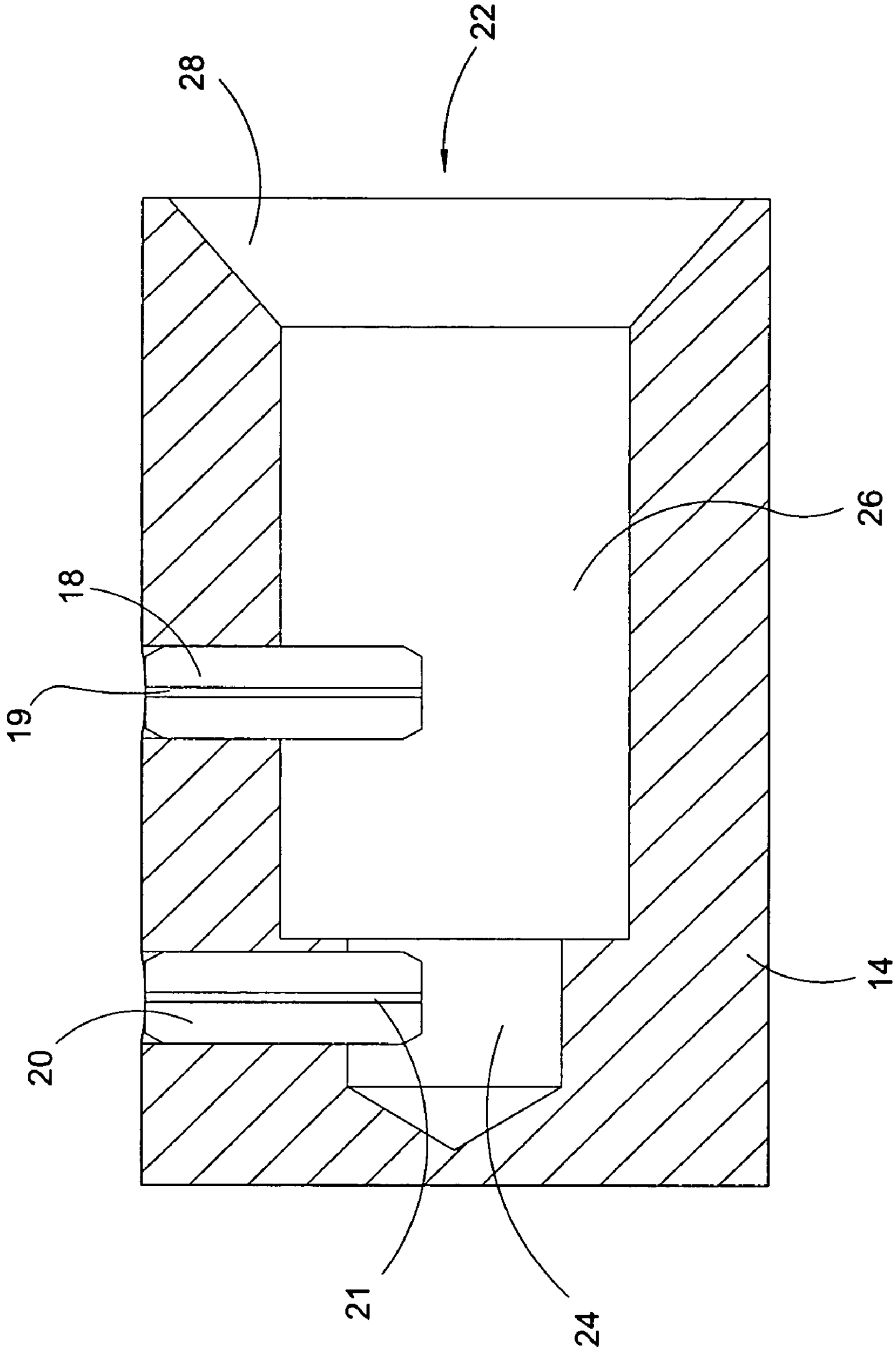
FIG. 3 is a sectional view as indicated in FIG. 2.
Figure 4:
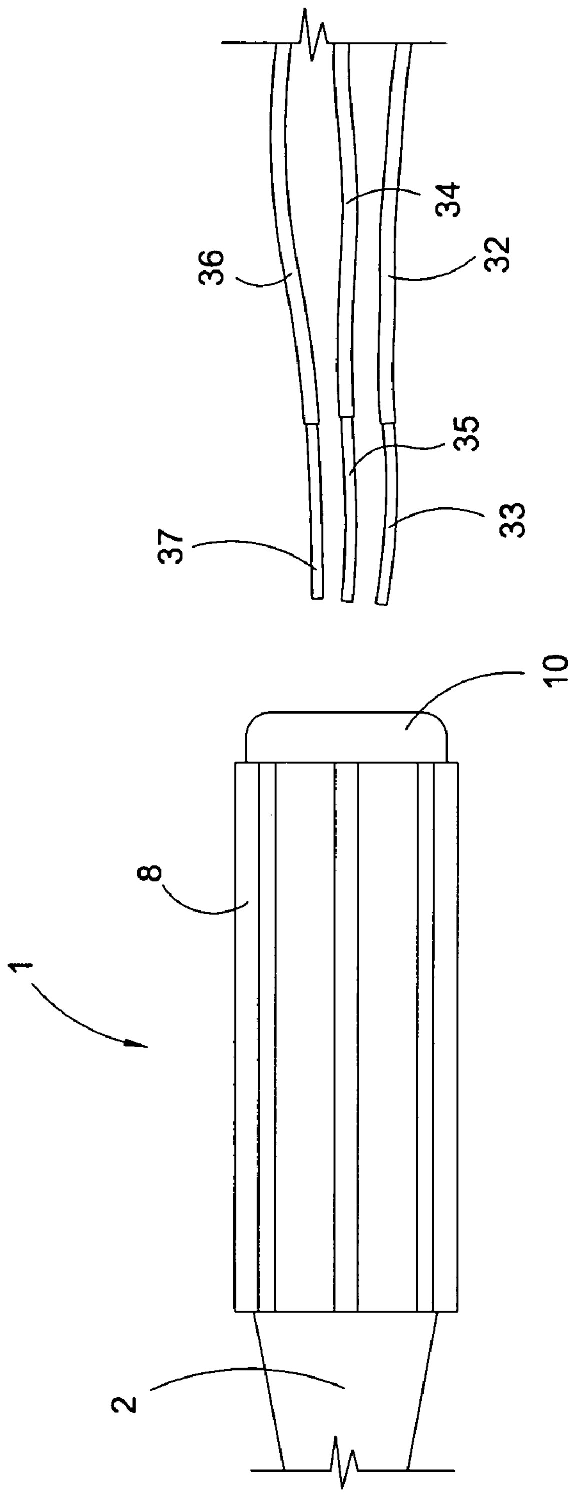
FIG. 4 is a partial side view of the tool of FIG. 1, the view additionally showing electrical wiring ready for insertion.

Referring simultaneously to FIGS. 2 and 3, the socket 14 is preferably composed of steel or aluminum, and preferably includes a second rearwardly opening bore 22 which extends forwardly into the socket 14 from the socket's rear end. Said second rearwardly opening bore 22 is preferably annularly coffered to present a forward narrow diameter wire receiving section 24, an intermediate wide diameter wire receiving section 26, and a rearward chamfered or angularly coffered wire insertion guiding section 28.

Referring further simultaneously to FIGS. 2 and 3, traction pins 18 and 20 preferably respectively extend radially inwardly into the narrow and wide sections 24 and 26 of bore 22, such pins preferably being nestingly received within radially opening and extending pin receiving channels. The traction pins 18 and 20 preferably comprise compression or spring biasing roll pins, each having a spring biasing gap 19 and 20, and each having a "C" shaped cross-sectional profile. Such traction pins 18 and 20 advantageously spring bias against their receiving channels for permanent and fixed mounting upon the socket 14.

Figure 5:
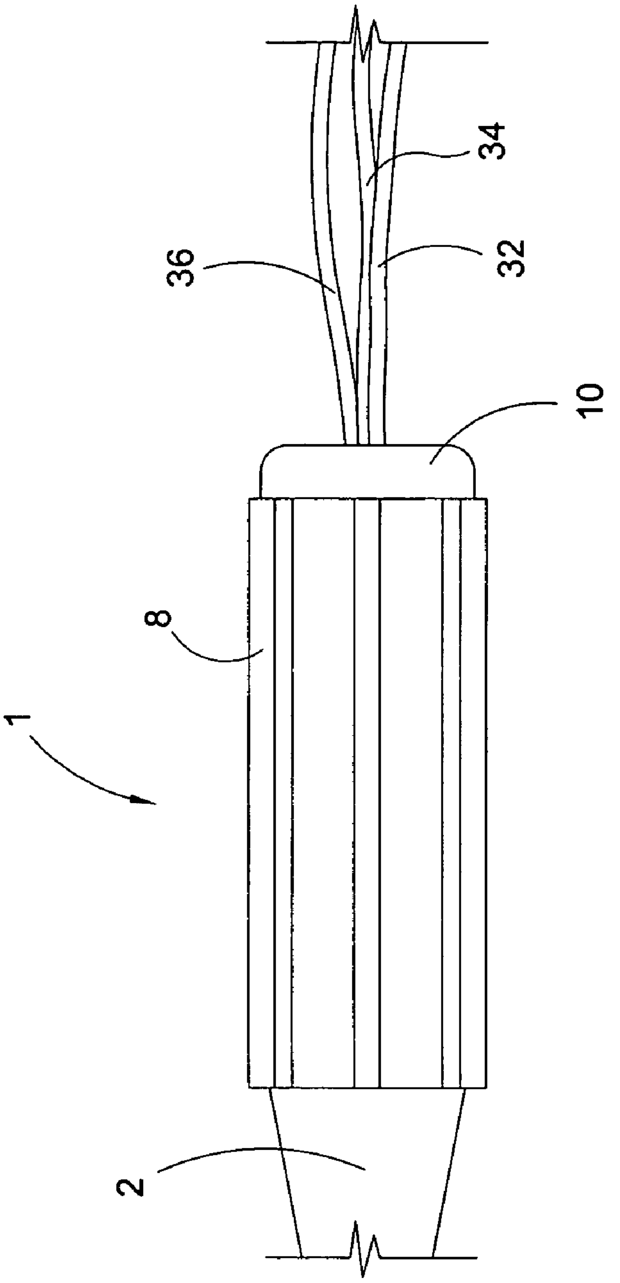
FIG. 5 redepicts FIG. 4, the view showing electrical wiring inserted.

In use of the instant inventive wire twisting driver tool, referring simultaneously to FIGS. 1-3, an electrician may grasp handle 2 in his or her left hand while grasping the insulated electrical wires 32, 34, and 36 in his or her right hand. Preferably, the electrician has preliminarily stripped the insulation from the ends of wires 32, 34, and 36, exposing stripped aluminum or cooper wire ends 33, 35, and 37. Thereafter, referring further simultaneously to FIG. 5, the electrician may move the wires 32, 34, and 36 forwardly toward the rear end 10 of the handle 2, causing the extreme forward ends of wires 32, 34, and 36 to enter the chamfered wire guiding section 28 of the rearwardly opening bore 22. Upon further forward motion of wires 32, 34, and 36 with respect to the handle 2, the chamfered walls of section 28 initially guide the wires into the large diameter section 26 of the rearwardly opening bore 22. In the event that the cumulative cross-sectional profiles of wire ends 33, 35, and 37 are small enough to fit within the cross-sectional profile of the forward bore section 24, such wire ends will continue to forwardly extend beyond the annular coffer which divides sections 24 and 26. Conversely, in the event that the cumulative cross-sectional profiles of wire ends 33, 35, and 37 are too great to fit within the forward bore section 24, the face of the annular coffer will stop such forward insertion.

Regardless of the bore section 24 or 26 within which the forward ends of wire ends 33, 35, and 37 finally rest, at least one of the traction pins 18 and 20 will engage the stripped wire ends 33, 35, and 37, such pin or pins extending interstitially between a pair of wire ends among such wire ends.

Figure 6:
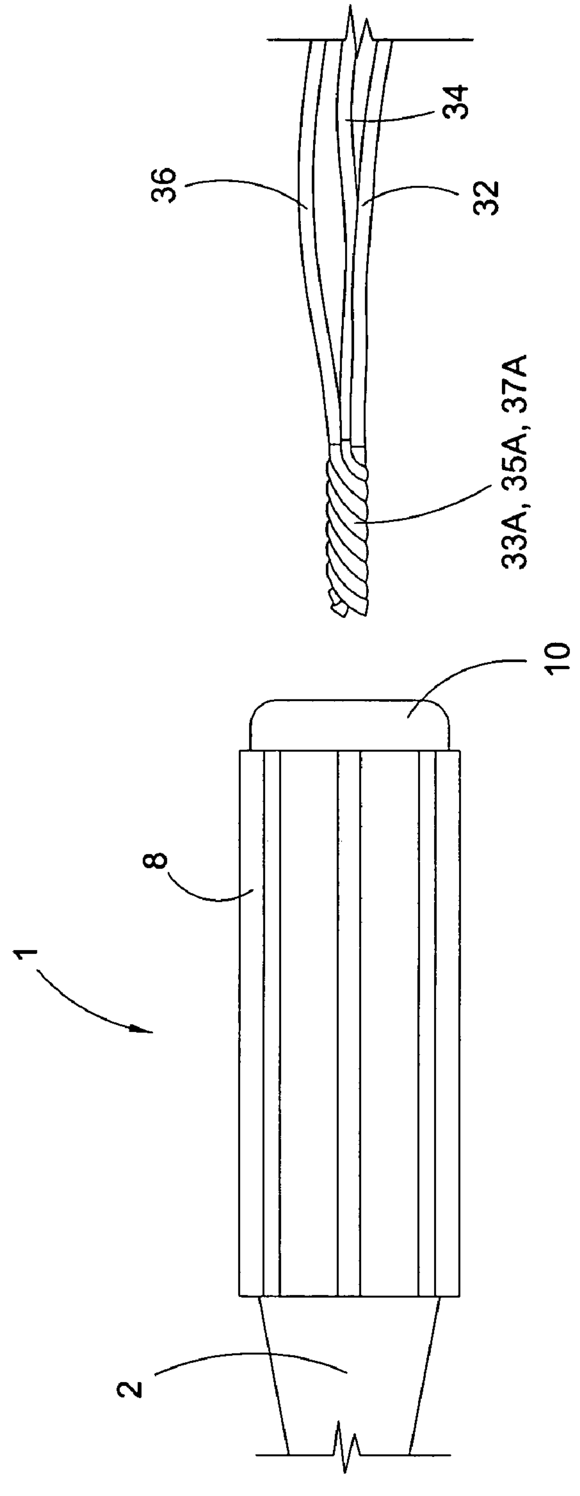
FIG. 6 redepicts FIG. 5, the view showing electrical wiring rearwardly extracted and helically intertwined and interconnected.

Referring further simultaneously to FIGS. 1-5, upon complete insertion of the bundle of wires 32, 34, and 36 into the bore 22 of socket 14, the electrician preferably right-handedly rotates such wires with respect to handle 2. Upon such right-handed rotation, traction pin 18 or both traction pins 18 and 20, as the case may be, engagingly bias against stripped wire ends 33, 35, and 37, and apply left-handed rotational torque to the stripped wire ends 33, 35, and 37, left-handedly and helically intertwining and interconnecting such wire ends about themselves. Thereafter, referring further simultaneously to FIG. 6, such electrician may rearwardly withdraw wires 32, 34, and 36, exposing a new helically intertwined and left-handedly twisting wire tail 33A, 35A, and 37A. Thereafter, the electrician may apply a right-handed insulating twist-on wire connector (not depicted) to such wire tail 33A, 35A, and 37A. Tightening of such right-handed twist-on wire connector tends to further helically intertwine the wires of tail 33A, 35A, and 37A.

Referring simultaneously to all figures, by using the instant inventive wire twisting driver tool 1, an electrician may conveniently utilize the singular tool for manipulating screw and nut electrical terminal connections, and for creating wire nut protected electrical connections without changing hand tools.

While the principles of the invention have been made clear in the above illustrative embodiment, those skilled in the art may make modifications in the structure, arrangement, portions and components of the invention without departing from those principles. Accordingly, it is intended that the description and drawings be interpreted as illustrative and not in the limiting sense, and that the invention be given a scope commensurate with the appended claims.

I claim:

1. A driver comprising:

(a) a handle having front and rear ends;

(b) a driver shaft having front and rear ends, the driver shaft being fixedly attached to or formed wholly with the handle, the driver shaft extending forwardly from the front end of the handle;

(c) a driver fixedly attached to or wholly formed with the front end of the driver shaft, the driver head being selected from the group consisting of common screw driving heads, phillips screw driving heads, and nut driving sockets;

(d) a rearwardly opening wire and receiving bore extending forwardly into the handle from the rear end of the handle, the rearwardly opening wire end receiving bore having a closed forward end;

(e) at least a first traction pin fixedly attached to or formed wholly with the handle, the at least first traction pin having an inner end, the inner end of the at least first traction pin extending radially into the rearwardly opening bore, the inner end of the at least first traction pin terminating within the rearwardly opening bore.

2. The driver of claim 1 wherein the handle is annularly stratified, the handle's strata comprising an inner stratum and an outer stratum, the inner stratum extending annularly about the wire end receiving rearwardly opening bore.

3. The driver of claim 2 wherein the wire and receiving rearwardly opening bore is annularly coffered.

4. The driver of claim 3 further comprising at least a second traction pin fixedly attached to or formed wholly with the handle, the at least second traction pin having an inner end, the inner end of the at least second traction pin extending radially into the wire end receiving rearwardly opening bore, the at least first and at least second traction pins being respectively positioned forwardly from and rearwardly from the wire end receiving rearwardly opening bore's annular coffer.

5. The driver of claim 2 wherein the inner stratum comprises metal, and wherein the outer stratum is dielectric.

6. The driver of claim 5 wherein the handle's inner stratum has a front end, the inner stratum's front end being positioned rearwardly from the rear end of the driver shaft.

7. The driver of claim 6 wherein the wire end receiving rearwardly opening bore is annularly coffered.

8. The driver of claim 7 further comprising at least a second traction pin fixedly attached to or formed wholly with the handle, the at least second traction pin having an inner end, the inner end of the at least second traction pin extending radially into the wire end receiving rearwardly opening bore, the at least first and at least second traction pins being respectively positioned forwardly from and rearwardly from the wire end receiving rearwardly opening bore's annular coffer.

9. A driver comprising:

(a) a handle having front and rear ends;

(b) a driver shaft having front and rear ends, the driver shaft being fixedly attached to or formed wholly with the handle, the driver shaft extending forwardly from the front end of the handle;

(c) a driver head fixedly attached to or formed wholly with the front end of the driver shaft, the driver head being selected from the group consisting of common screw driving heads, phillips screw driving heads, and nut driving sockets;

(d) a first rearwardly opening bore extending forwardly into the handle from the rear end of the handle;

(e) a socket having front and rear ends, the socket being nestingly received within the first rearwardly opening bore;

(f) a second rearwardly opening wire end receiving bore extending forwardly into the socket from its rearward end, the second rearwardly opening wire end receiving bore having a closed forward end;

(g) at least a first radially opening bore extending radially outward from the second rearwardly opening bore; and (h) at least a first traction pin nestingly received by and extending radially inwardly from the at least first radially opening bore, the at least first traction pin having an end terminating within the second rearwardly opening wire end receiving bore.

10. The driver of claim 9 wherein the second rearwardly opening wire end receiving bore is annularly coffered.

11. The driver of claim 10 further comprising at least a second radially opening bore extending radially outwardly from the second rearwardly opening wire end receiving bore, and at least a second traction pin, the at least second traction pin being nestingly received by and extending radially inwardly from the at least second radially opening bore, the at least first and at least second radially opening bores and their nestingly received at least first and at least second traction pins being respectively positioned forwardly from and rearwardly from the second rearwardly opening wire end receiving bore's annular coffer.

12. The driver of claim 11 wherein the socket comprises metal and wherein the handle is dielectric.

13. The driver of claim 12 wherein the socket has a front end, the socket's front end being positioned rearwardly from the rear end of the driver shaft.

14. The driver of claim 13 wherein the at least first and at least second traction pins comprise roll pins, the respective nesting receipts of the at least first and at least second traction pins within the at least first and at least second radially opening bores comprising compression fittings.

* * * * *